US010041945B2

(12) United States Patent
Rengarajan et al.

(10) Patent No.: US 10,041,945 B2
(45) Date of Patent: Aug. 7, 2018

(54) METHODS OF DIAGNOSING AND TREATING TUBERCULOSIS (71) Applicant: Emory University, Atlanta, GA (US)

(72) Inventors: Jyothi Rengarajan, Decatur, GA (US); Toidi Adekambi, Atlanta, GA (US); Christian C. Ibegbu, Stockbridge, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 15/309,403

(22) PCT Filed: May 5, 2015

(86) PCT No.: PCT/US2015/029160
§ 371 (c)(1),
(2) Date: Nov. 7, 2016

(87) PCT Pub. No.: WO2015/171552
PCT Pub. Date: Nov. 12, 2015

(65) Prior Publication Data
US 2017/0082623 A1    Mar. 23, 2017

Related U.S. Application Data (60) Provisional application No. 61/988,406, filed on May 5, 2014.

(51) Int. Cl.
C12Q 1/00      (2006.01)
G01N 33/569    (2006.01)
A61K 31/4965   (2006.01)
A61K 45/06     (2006.01)
A61K 31/133    (2006.01)
A61K 31/4409   (2006.01)
A61K 31/496    (2006.01)
G01N 33/50     (2006.01)

(52) U.S. Cl.
CPC ..... G01N 33/56972 (2013.01); A61K 31/133 (2013.01); A61K 31/4409 (2013.01); A61K 31/496 (2013.01); A61K 31/4965 (2013.01); A61K 45/06 (2013.01); G01N 33/5091 (2013.01); G01N 2333/35 (2013.01); G01N 2333/47 (2013.01); G01N 2333/57 (2013.01); G01N 2333/70514 (2013.01); G01N 2333/70539 (2013.01); G01N 2333/70596 (2013.01); G01N 2800/26 (2013.01)

(58) Field of Classification Search
CPC .............................................. G01N 33/56972
See application file for complete search history.

(56) References Cited

U.S. PATENT DOCUMENTS

2014/0080732 A1    3/2014  Banchereau
2014/0378425 A1   12/2014  Wilde

OTHER PUBLICATIONS

Mahan et al (PLoS ONE vol. 5, Issue 2, pp. 1-6, 2010).*
Adekambi et al. Biomarkers on patient T cells diagnose active tuberculosis and monitor treatment response, J Clin Invest, 2015,125(5):1827-38.
Berry et al. An interferon-inducible neutrophil-driven blood transcriptional signature in human tuberculosis, Nature, 2010, 466(7309): 973-977.
Bloom et al. Transcriptional Blood Signatures Distinguish Pulmonary Tuberculosis, Pulmonary Sarcoidosis, Pneumonias and Lung Cancers, PLoS ONE, 2013, 8(8): e70630.
Dintwe et al. Heterologous vaccination against human tuberculosis modulates antigen-specific CD4+ T-cell function, Eur. J. Immunol. 2013. 43: 2409-2420.
Janossy, The changing pattern of "smart" flow cytometry (S-FC) to assist the cost-effective diagnosis of HIV, tuberculosis, and leukemias in resource-restricted conditions, Biotechnol. J. 2008, 3, 32-42.
Janssens et al. Quantitative scoring of an interferon-c assay for differentiating active from latent tuberculosis, Eur Respir J, 2007; 30: 722-727.
Lancioni et al. Effects of Antiretroviral Therapy on Immune Function of HIV-infected Adults with Pulmonary Tuberculosis and CD4 + >350 Cells/mm3, J Infect Dis. 2011, 203(7): 992-1001.
Mahan et al. Tuberculosis Treatment in HIV Infected Ugandans with CD4 Counts .350 Cells/mm3 Reduces Immune Activation with No Effect on HIV Load or CD4 Count, PLoS ONE, 2009, 5(2): e9138.
Morris et al. Human Immunodeficiency Virus-1 RNA Levels and CD4 Lymphocyte Counts, during Treatment for Active Tuberculosis, in South African Patients, The Journal of Infectious Diseases, 2003,187:1967-71.
Ngai et al. Gamma Interferon Responses of CD4 and CD8 T-Cell Subsets Are Quantitatively Different and Independent of Each Other during Pulmonary Mycobacterium bovis BCG Infection, Infect Immun. 2007, 75(5): 2244-2252.
Riou et al. A Subset of Circulating Blood Mycobacteria-Specific CD4 T Cells Can Predict the Time to Mycobacterium tuberculosis Sputum Culture Conversion, PLoS ONE, 2014, 9(7): e102178.
Rodrigues et al. Immunophenotypic characterization of peripheral T lymphocytes in Mycobacterium tuberculosis infection and disease, Clin Exp Immunol, 2002, 128:149-154.
Shanker et al. Mechanistic insights on immunosenescence and chronic immune activation in HIV-tuberculosis co-infection, World J Virol, 2015, 4(1): 17-24.
Siawaya et al. Correlates for disease progression and prognosis during concurrent HIV/TB infection, International Journal of Infectious Diseases (2007) 11, 289-299.

(Continued)

Primary Examiner — Albert M Navarro
(74) Attorney, Agent, or Firm — EmoryPatent Group (57) ABSTRACT This disclosure relates to methods of treating and diagnosing a tuberculosis infection as pulmonary active or latent based on biomarkers expressed on pools of CD4+ cells. In certain embodiments, the disclosure relates to methods of treatment of a subject diagnosed with tuberculosis comprising the steps of, measuring a pool of CD4 IFN-γ cells for cells that also express CD38, HLA-DR, and/or Ki-67 providing a measurement; associating an increased measurement of CD4 IFN-γ cells that also express CD38, HLA-DR, Ki-67, compared to a control, as an indication that the subject has active tuberculosis; and treating the subject with an aggressive tuberculosis treatment.

8 Claims, 10 Drawing Sheets (56) References Cited

OTHER PUBLICATIONS

Silva et al. T Cell Activation and Cytokine Profile of Tuberculosis and HIV-Positive Individuals during Antituberculous Treatment and Efavirenz-Based Regimens, PLoS ONE, 2013 8(6): e66095.

Soares et al. Novel application of Ki67 to quantify antigen-specific in vitro lymphoproliferation, Journal of Immunological Methods, 362 (2010) 43-50.

Socorro et al. Distribution of Naive and Memory/Effector CD4+ T Lymphocytes and Expression of CD38 on CD8 + T Lymphocytes in AIDS Patients With Tuberculosis, The Brazilian Journal of Infectious Diseases, 2003, 7(2):161-165.

Urdahl et al. Initiation and regulation of T-cell responses in tuberculosis, Mucosal Immunol. 2011, 4(3): 288-293.

Vigano et al. Expression of CD38 on CD8 T cells predicts maintenance of high viraemia in HAART-treated HIV-1-infected children, Lancet. 1998, 352(9144):1905-6.

Wallis et al. Biomarkers for tuberculosis disease activity, cure, and relapse, Lancet Infect Dis. 2009, 9(3):162-72.

\* cited by examiner

METHODS OF DIAGNOSING AND TREATING TUBERCULOSIS

CROSS-REFERENCE TO RELATED APPLICATIONS

This application claims the benefit of priority to U.S. Provisional Application No. 61/988,406 filed May 5, 2014, which application is hereby incorporated by reference in its entirety.

STATEMENT REGARDING FEDERALLY FUNDED RESEARCH

This invention was made with government support under Grant GS123456 awarded by the National Institutes of Health. The Government has certain rights in the invention.

BACKGROUND

A human infected with *mycobacterium tuberculosis* (Mtb) may be a hidden because an individual is asymptomatic. Someone with an active tuberculosis infection typically shows symptoms of a chronic cough and blood-tinged sputum referred to as a pulmonary active tuberculosis (ATB) infection. The asymptomatic or latent tuberculosis infections (LTBI) often do not progress to ATB for an individual with a healthy immune system. However, those with a compromised immune system, such as the elderly and those with HIV, have a much higher chance of developing life threatening ATB.

The standard treatment regimen for drug-susceptible TB consists of a 2-month intensive phase with isoniazid, rifampicin, pyrazinamide, and ethambutol (HRZE), followed by a 4-month continuation phase with isoniazid and rifampicin (HR). Conversion to a negative sputum culture after treatment initiation is currently the most objective indicator of response to treatment; however, this method takes 3 to 6 weeks for results. Additionally, sputum smears are not highly accurate with a high proportion of tuberculosis (TB) cases resulting in false negatives. Nucleic acid amplification-based tests are more sensitive, but do not differentiate between live and dead Mtb limiting the effectiveness in monitoring treatment-mediated clearance of Mtb. Existing blood-based tests, such as IFN-γ release assays (IGRAs), measure IFN-$\gamma^+$ production in response to stimulation with Mtb-specific antigens ESAT6 and CFP10 and are specific for Mtb infection. However, IGRAs (e.g., QuantiFERON or T-SPOT.TB) do not discriminate between ATB and latent Mtb infection (LTBI) and are inadequate for monitoring treatment response. Thus, there is a need for identifying improved ways of monitoring the effectiveness of TB treatment.

Vigano et al. report expression of CD38 on CD8 T cells predicts maintenance of high viraemia in HAART-treated HIV-1-infected children. Highly active antiretroviral therapy, Lancet, 1998, 352(9144):1905-1906.

Janssens et al. report quantitative scoring of an interferon-γ assay for differentiating active from latent tuberculosis. Eur Respir J, 2007, 30(4):722-728.

Wallis et al. report biomarkers for tuberculosis disease activity, cure, and relapse. Lancet Infect Dis, 2009, 9(3): 162-172.

Berry et al. report an interferon-inducible neutrophil-driven blood transcriptional signature in human tuberculosis. Nature, 2010, 466(7309):973-977.

Bloom et al. report transcriptional blood signatures distinguish pulmonary tuberculosis, pulmonary sarcoidosis, pneumonias and lung cancers. PLoS One, 2013, 8(8): e70630.

Riou et al. report a subset of circulating blood mycobacteria-specific CD4 T cells can predict the time to *Mycobacterium tuberculosis* sputum culture conversion. PLoS One, 2014, 9(7):e102178.

References cited herein are not an admission of prior art.

SUMMARY

This disclosure relates to methods of treating and diagnosing a tuberculosis infection as pulmonary active or latent based on biomarkers expressed on pools of $CD4^+$ cells. In certain embodiments, the disclosure relates to methods of treatment of a subject diagnosed with tuberculosis comprising the steps of, measuring a pool of CD4 IFN-γ cells for cells that also express CD38, HLA-DR, and/or Ki-67 providing a measurement; associating an increased measurement of CD4 IFN-γ cells that also express CD38, HLA-DR, Ki-67, compared to a control, as an indication that the subject has active tuberculosis; and treating the subject with an aggressive tuberculosis treatment.

In certain embodiments, the increased measurement of CD4 IFN-γ cells that also express CD38, HLA-DR, Ki-67, compared to a control is a quantification that, greater than 18% of the CD4 IFN-γ cells also express CD38; greater than 60% of the CD4 IFN-γ cells also express HLA-DR; and greater than 5% of the CD4 IFN-γ cells also express Ki-67.

In certain embodiments, the aggressive tuberculosis treatment comprises administering a combination of more than two antibacterial agents optionally in combination with a corticosteroid such as dexamethasone. In certain embodiments, the aggressive tuberculosis treatment comprises administering a combination of isoniazid, rifampicin, pyrazinamide, and ethambutol. In certain embodiments, the aggressive tuberculosis treatment comprises administering meropenem and clavulanic acid in combination with one or more additional antibiotic agents.

In certain embodiments, the methods further comprising the steps of, measuring a second pool of CD4 IFN-γ cells for the quantity of cells that also express CD38, HLA-DR, and Ki-67; associating an deceased measurement of CD4 IFN-γ cells that also express CD38, HLA-DR, Ki-67, compared to the increased measurement, as an indication that the subject has a latent tuberculosis infections; and treating the subject with an less aggressive tuberculosis treatment.

In certain embodiments, the less aggressive tuberculosis treatment is only one or not more than a combination of two antibacterial agents. In certain embodiments, the less aggressive tuberculosis treatment is a combination of only isoniazid and rifampicin.

In certain embodiments, the measurement, quantification, or indication is recorded on a computer readable medium. In certain embodiments, the measurement, quantification, or indication is communicated to a medical professional or the subject.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

In this specification and in the claims that follow, reference will be made to a number of terms that shall be defined to have the following meanings unless a contrary intention is apparent.

Prior to describing the various embodiments, the following definitions are provided and should be used unless otherwise indicated.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, prostate tissue, blood, blood plasma, urine, or cerebral spinal fluid (CSF).

"Subject" means any animal, but is preferably a mammal, such as, for example, a human, monkey, mouse, or rabbit.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Proteins Expressed on Patient CD4 T Cells Diagnose Active Tuberculosis and Monitor Treatment Response Studies in chronic viral infections have shown that the phenotypes and frequencies of virus-specific $CD4^+$ and $CD8^+$ T cell phenotypes correlate with viral antigen load in vivo. There is a substantial burden of replicating mycobacteria present in ATB. Human CD38 is a transmembrane glycoprotein that is expressed in a wide array of immune cell types. CD38 has ectoenzyme properties, catalyzing the synthesis and hydrolysis of NAD or cyclic ADP-ribose, and its expression is highly induced on the surface of antigen-specific effector T cells. HLA-DR is an MHC class II cell-surface receptor involved in antigen presentation, which is highly expressed on activated antigen-specific T cells. Both CD38 and HLA-DR are early immune markers that reflect T cell activation in response to microbial infection or vaccination. Ki-67 is a nuclear protein that has been widely used as an intracellular proliferation marker due to its selective expression in cycling cells.

$CD38^+IFN-\gamma^+$, $HLA-DR^+IFN-\gamma^+$, and $Ki-67^+IFN-\gamma^+CD4^+$ T cells each distinguished individuals with LTBI from treatment-naive individuals with sputum culture-confirmed ATB recruited from the metropolitan Atlanta area. These markers also accurately classified individuals with ATB and LTBI recruited from the Western Cape in South Africa. These markers are associated with responsiveness to anti-TB treatment and clinical resolution of TB.

$CD4^+$ T cells expressing $IFN-\gamma^+$ clearly play an important role in controlling Mtb replication and containing bacteria within lung granulomas. Humans with IFN-γ receptor abnormalities show increased susceptibility to mycobacterial diseases. However, IFN-γ responses are not indicative of immune control in TB, and Mtb-specific $IFN-\gamma^+CD4^+$ T cells do not distinguish between active and latent TB. Studies herein validate the inability of Mtb-specific IFN-γ production alone or CD38, HLA-DR, and Ki-67 expression alone on bulk $CD4^+$ T cells to discriminate between ATB and LTBI and monitor decreasing bacterial loads. This underscores the utility of phenotypic markers expressed on Mtb-specific $CD4^+$ T cells as biomarkers for diagnosing TB. Individuals with ATB disease harbor higher frequencies of activated ($CD38^+$, $HLA-DR^+$), cycling ($Ki-67^+$) T cells than those with LTBI. Mtb-specific effector memory $CD4^+$ T cells in individuals with LTBI exhibited a resting, nonactivated phenotype and were largely noncycling. In the present study, the immune activation markers CD38 and HLA-DR and the intracellular proliferation marker Ki-67 were identified on Mtb-specific $IFN-\gamma^+CD4^+$ T cells as biomarkers that discriminate between ATB and LTBI with high sensitivity, specificity, and predictive value in a US-based cohort. the ability of these biomarkers to accurately classify ATB and LTBI in an independent cohort from South Africa, where the investigators were blinded to the clinical diagnoses until after completion of the laboratory analyses was further validated. Thus, phenotypic biomarkers that provide discriminatory capacity to $IFN-\gamma^+$-based assays are identified.

While CD38, HLA-DR, and Ki-67 expression on Mtb-specific $CD4^+$ T cells distinguished individuals with LTBI from ATB patients, examining expression levels of these biomarkers on Mtb-specific $CD8^+$ T cells was less useful. This is due to low-to-undetectable frequencies of $CD8^+$ $IFN-\gamma^+$ T cells in individuals with LTBI and ATB. Thus, unlike with $CD4^+IFN-\gamma^+$ T cells, phenotyping the $CD8^+$ $IFN-\gamma^+$ T cells for expression of CD38, HLA-DR, and Ki-67 was not possible for the majority of LTBI samples. Therefore, Mtb-specific $CD4^+$ T cells provided the optimal biomarker signatures.

Frequencies of CD38-, HLA-DR-, and Ki-67-expressing Mtb-specific $CD4^+$ T cells correlate with Mtb burden in vivo and mirror sputum conversion during anti-TB treatment, providing real-time readouts for monitoring a patient's responsiveness to treatment.

Expression of the costimulatory molecule CD27 on Mtb-specific T cells was recently shown to have predictive value in distinguishing active and latent TB; however, $CD27^+$ $IFN-\gamma^+CD4^+$ T cell frequencies were not evaluated in the context of monitoring treatment response in longitudinal studies.

Frequencies of $CD38^+IFN-\gamma^+$, $HLA-DR^+IFN-\gamma^+$, and $Ki-67^+IFN-\gamma^+$ Mtb-specific T cells were comparable to those in the LTBI group in all 10 patients who successfully resolved TB after 6 months of anti-TB treatment. Our data also showed that these biomarkers correlated with Mtb load and mirrored sputum conversion during the course of anti-TB treatment, suggesting that these biomarkers may also prove useful for diagnosing culture-negative individuals with clinical symptoms of TB, for whom clinical response to treatment is currently used as diagnosis. While the 6-month treatment duration is recommended as the standard regimen for treating ATB, longer regimens are required when sputum conversion is delayed beyond the 2-month milestone. Shortening treatment from 6 to 4 months in patients with drug-susceptible Mtb in a TB-endemic area resulted in higher relapse rates. In this context, blood-based biomarkers have the potential to more rapidly identify delayed responsiveness or non-responsiveness to anti-TB treatment (e.g., in patients infected with drug-resistant strains) compared with sputum culture and may predict sputum conversion. Notably, $CD38^+$ $IFN-\gamma^+$, $HLA-DR^+IFN-\gamma^+$, and $Ki-67^+IFN-\gamma^+$ T cell frequencies were below the discriminatory cutoffs for ATB and LTBI after 4 months of anti-TB treatment. Thus, in certain embodiments, the disclosure contemplates measuring for lower levels of $CD38^+IFN-\gamma^+$, $HLA-DR^+IFN-\gamma^+$, and $Ki-67^+$ $IFN-\gamma^+$ T cells and changing or terminating the therapeutic treatments, e.g., in four months or less. Four months of anti-TB treatment may be sufficient for some patients with drug-susceptible TB.

Frequencies of $CD38^+IFN-\gamma^+$, $HLA-DR^+IFN-\gamma^+$, or $Ki-67^+IFN-\gamma^+$ expression on Mtb-specific $CD4^+$ T cells have the potential to accurately diagnose ATB and discriminate between ATB and LTBI is contemplated in extra-pulmonary TB and HIV/TB co-infection. Flow cytometry-based tests involving host biomarkers identified here are likely to be particularly useful in situations where obtaining a sputum specimen is difficult, e.g., in children and weakened patients. Overall, Mtb-specific $CD38^+IFN-\gamma^+$, $HLA-DR^+IFN-\gamma^+$, and $Ki-67^+IFN-\gamma^+CD4^+$ T cells show potential as biomarkers for diagnosing ATB. Moreover, they provide a gauge of Mtb load in vivo, suggesting utility as surrogate markers of treatment response and as predictors of treatment efficacy, cure, and relapse in patients undergoing anti-TB treatment for drug-susceptible as well as drug-resistant TB and in clinical trials evaluating efficacy of new therapeutics.

In certain embodiments, the disclosure relates to methods of treatment of a subject diagnosed with tuberculosis comprising the steps of, measuring a pool of CD4$^+$IFN-γ cells for cells that also express CD38, HLA-DR, and/or Ki-67 providing a measurement; associating an increased measurement of CD4$^+$IFN-γ cells that also express CD38, HLA-DR, Ki-67, compared to a control, as an indication that the subject has active tuberculosis; and treating the subject with an aggressive tuberculosis treatment.

In certain embodiments, the increased measurement of CD4$^+$IFN-γ cells that also express CD38, HLA-DR, Ki-67, compared to a control is a quantification that, greater than 18% of the CD4$^+$IFN-γ cells also express CD38; greater than 60% of the CD4$^+$IFN-γ cells also express HLA-DR; and greater than 5% of the CD4$^+$IFN-γ cells also express Ki-67.

In certain embodiments, the aggressive tuberculosis treatment comprises administering a combination of more than two antibacterial agents optionally in combination with a corticosteroid such as dexamethasone. In certain embodiments, the aggressive tuberculosis treatment comprises administering a combination of isoniazid, rifampicin, pyrazinamide, and ethambutol. In certain embodiments, the aggressive tuberculosis treatment comprises administering meropenem and clavulanic acid in combination with one or more additional antibiotic agents.

In certain embodiments, the methods further comprising the steps of, measuring a second pool of CD4$^+$IFN-γ cells for the quantity of cells that also express CD38, HLA-DR, and Ki-67; associating an deceased measurement of CD4$^+$IFN-γ cells that also express CD38, HLA-DR, Ki-67, compared to the increased measurement, as an indication that the subject has a latent tuberculosis infections; and treating the subject with an less aggressive tuberculosis treatment.

In certain embodiments, the less aggressive tuberculosis treatment is only one or not more than a combination of two antibacterial agents. In certain embodiments, the less aggressive tuberculosis treatment is a combination of only isoniazid and rifampicin.

In certain embodiments, the measurement, quantification, or indication is recorded on a computer readable medium. In certain embodiments, the measurement, quantification, or indication is communicated to a medical professional or the subject.

The term "antibacterial" or "antibiotic" agent refers to molecules that may either kill or inhibit the growth of bacteria. In certain embodiments, the antibiotic is selected from the group comprising of sulfonamides, diaminopyrimidines, quinolones, beta-lactam antibiotics, cephalosporins, retracyclines, nitrobenzene derivatives, aminoglycosides, macrolide antibiotics, polypeptide antibiotics, nitrofuran derivatives, nitroimidazoles, nicotinin acid derivatives, polyene antibiotics, imidazole derivatives or glycopeptide, cyclic lipopeptides, glycylcyclines and oxazolidinones. In further embodiments, these antibiotics include but are not limited to sulphadiazine, sulfones—[dapsone (DDS) and paraaminosalicyclic (PAS)], sulfanilamide, sulfamethizole, sulfamethoxazole, sulfapyridine, rrimethoprim, pyrimethamine, nalidixic acids, norfloxacin, ciproflaxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizole, cefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem) monobactams (aztreonam) oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomicin, neomycin, netilmicin, streptomycin, tobramycin, azithromycin, clarithromycin, dirithromycin, erythromycin, roxithromycin, telithromycin, polymyxin-B, colistin, bacitracin, tyrothricin notrifurantoin, furazolidone, metronidazole, tinidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, chloramphenicol, clindamycin, colistin, fosfomycin, loracarbef, metronidazole, nitrofurantoin, polymyxin B, polymyxin B sulfate, procain, spectinomycin, tinidazole, trimethoprim, ramoplanin, teicoplanin, vancomycin, trimethoprim, sulfamethoxazole, nitrofurantoin, prodrugs or alternative salts thereof.

In certain embodiments, the aggressive treatment comprises liposomes including agents selected from phosphatidylcholine (PC), L-α phosphatidic acid (PA) and cholesterol containing 4-(5-pentadecyl-1,3,4-oxadiazol-2-yl)pyridine.

Measurements

Flow cytometry is a laser based technique that may be employed in counting, sorting, and detecting cells by suspending particles in a stream of fluid and passing them by an electronic detection apparatus. A flow cytometer has the ability to discriminate different cells on the basis of color. Differential dyeing of cells emitting in different wavelengths, allows cells to be distinguished.

In certain embodiments, the disclosure relates to a blood based method of identifying and measuring cellular expression of proteins, e.g., CD4, IFN-γ, CD38, HLA-DR, and/or Ki-67 which utilizes an analytical platform. Although the measurements are exemplified utilizing flow cytometry, in certain embodiments, the disclosure contemplates alternative methods such as using a solid surface array comprising probes, e.g., CD4 antibodies, to proteins disclosed herein for the purpose of detecting and measuring them on the cells. Provided herein are devices for detection of cells expressing protein with surfaces comprising, attached thereto, at least one reagent specific for one or more proteins, e.g., CD4 and IFN-γ or CD38, HLA-DR, and Ki-67.

In certain embodiments, the cells can be immobilized to the surface by ligand binding and a detection reagent will bind specifically to the same protein or others on the exterior of the cell. The detection reagent may be conjugated to an enzyme to generate a signal that can be quantified. For example, Rica & Stevens report an enzyme label that controls the growth of gold nanoparticles and generates colored solutions with distinct tonality when the analyte is present. See Nature Nanotechnology, 2012, 7:821-824.

In certain embodiments, a cell may be captured with a ligand or antibody on a surface, and another protein on the cell surface is labeled with an enzyme. In one example, a detection antibody conjugated to biotin or streptavidin—to create a biotin-streptavidin linkage to an enzyme that contains streptavidin or biotin respectively. A signal is generated by the conversion of the enzyme substrate into a colored molecule and the intensity of the color of the solution is quantified by measuring the absorbance with a light sensor. Contemplated assays may utilize chromogenic reporters and substrates that produce some kind of observable color change to indicate the presence of the protein. Fluorogenic, electrochemiluminescent, and real-time PCR reporters are also contemplated to create quantifiable signals.

Although some assay formats will allow testing of peripheral biological fluid samples without prior processing of the sample, it is typical that peripheral biological fluid samples will be processed prior to testing. Processing generally takes the form of elimination of cells, such as platelets in blood samples, and may also include the elimination of certain proteins, such as certain clotting cascade proteins from blood. In some examples, the peripheral biological fluid sample is collected in a container comprising EDTA.

The process of comparing a measured value and normal or a reference value can be carried out in any convenient manner appropriate to the type of measured value and reference value for the protein at issue. As discussed above, measuring can be performed using quantitative or qualitative measurement techniques, and the mode of comparing a measured value and a reference value can vary depending on the measurement technology employed. For example, when a qualitative calorimetric assay is used to measure protein levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value. Alternately, a separate device (e.g., a digital computer) may be used to compare the measured value(s) and the reference value(s). Automated devices for comparison may include stored reference values for the protein(s) being measured, or they may compare the measured value(s) with reference values that are derived from contemporaneously measured reference samples.

In some embodiments, the methods of the disclosure utilize simple or binary comparison between the measured level(s) and the reference level(s) (e.g., the comparison between a measured level and a reference level determines whether the measured level is higher or lower than the reference level).

As described herein, biological fluid samples may be measured quantitatively (absolute values) or qualitatively (relative values). In certain aspects of the disclosure, the comparison is performed to determine the magnitude of the difference between the measured and reference values (e.g., comparing the fold or percentage difference between the measured value and the reference value).

EXPERIMENTAL

Higher Frequencies of Mtb-Specific $CD4^+$ T Cells Expressing CD38, HLA-DR, and Ki-67 in Subjects with ATB Compared with LTBI Individuals were recruited with LTBI and ATB in the metropolitan Atlanta area. LTBI subjects were identified based on a positive response to the Mtb-specific antigens ESAT6 and CFP10 upon screening their peripheral blood mononuclear cells (PBMCs) by IFN-γ ELISPOT assays. Patients with sputum culture-confirmed pulmonary TB disease were recruited at Grady Memorial Hospital prior to initiation of anti-TB treatment. Only patients with detectable IFN-γ responses to ESAT6/CFP10 peptide pools, as measured by flow cytometry, were included in the study. All 26 sputum-positive patients showed responses to cell wall (CW) antigens; of these, only 24 had detectable ESAT6/CFP10 responses. The activation profile of Mtb-specific $CD4^+$ T cells in these 24 ATB patients and 25 healthy subjects with LTBI was assessed by comparing the expression of CD38, HLA-DR, and Ki-67 on antigen-specific $CD4^+IFN-\gamma^+$ T cells in PBMCs from the ATB and LTBI groups by polychromatic flow cytometry after stimulation with Mtb-CW antigens and ESAT6/CFP10 peptide pools.

Figure 1A:
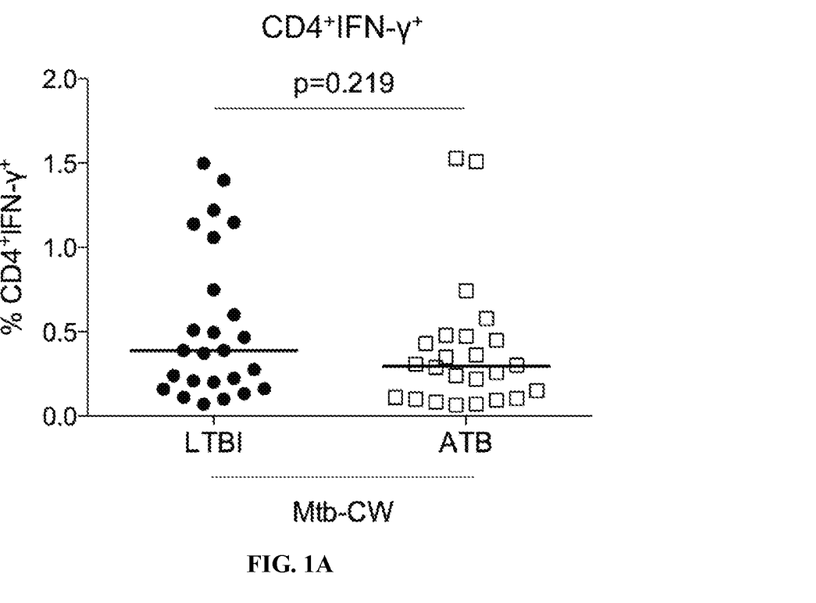
FIG. 1A shows data on IFN-$\gamma^+CD4^+$ T cells in the test cohort. PBMCs from individuals with LTBI (n=25) and treatment-naive ATB (n=24) were stimulated with Mtb-CW antigens
Figure 1B:
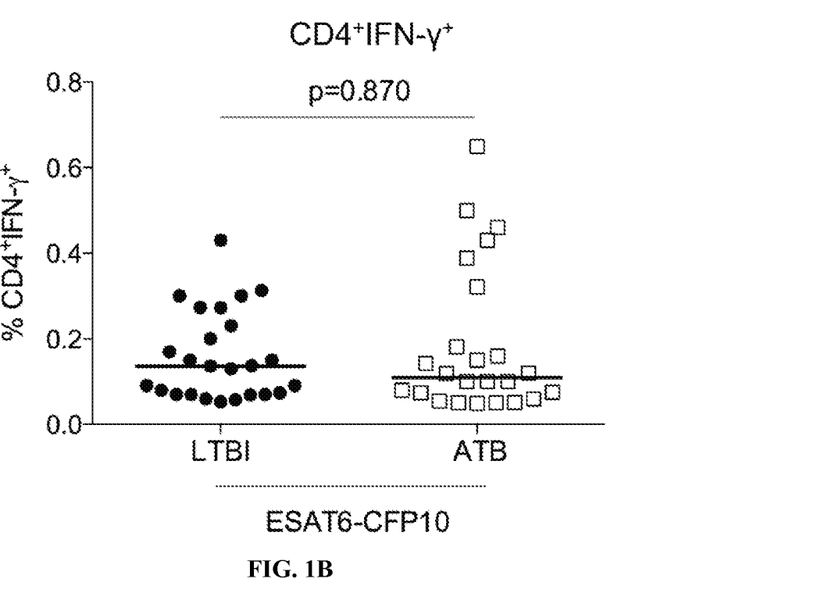
FIG. 1B shows individuals stimulated with ESAT6-CFP10 peptides.
Figure 2A:
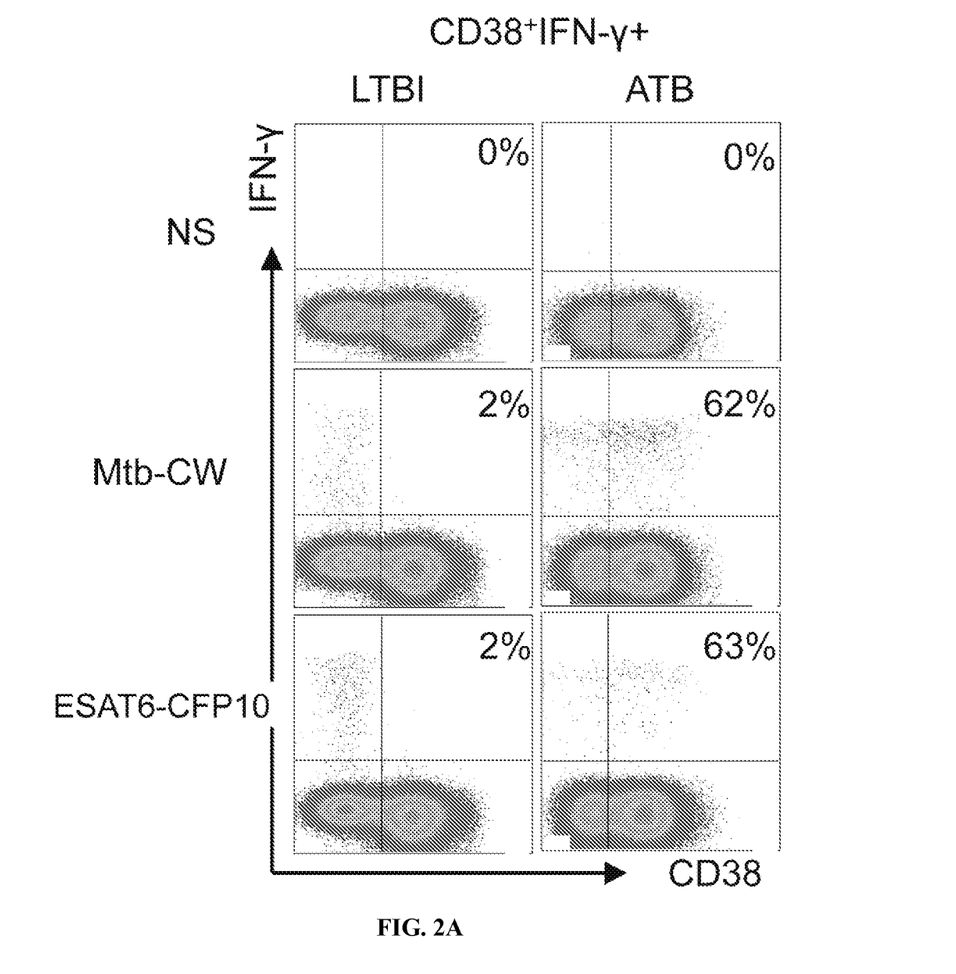
FIG. 2A shows data where PBMCs from individuals with LTBI (black circles, n=25) and ATB (white squares, n=24) were stimulated with Mtb-CW antigens and ESAT6-CFP10 peptide pools or non-stimulated (NS). The frequencies of activated Mtb-specific CD4$^+$ T cells were analyzed by flow cytometry. Representative flow plots for frequencies of CD38$^+$IFN-$\gamma^+$ T cells in LTBI and ATB groups.
Figure 2B:
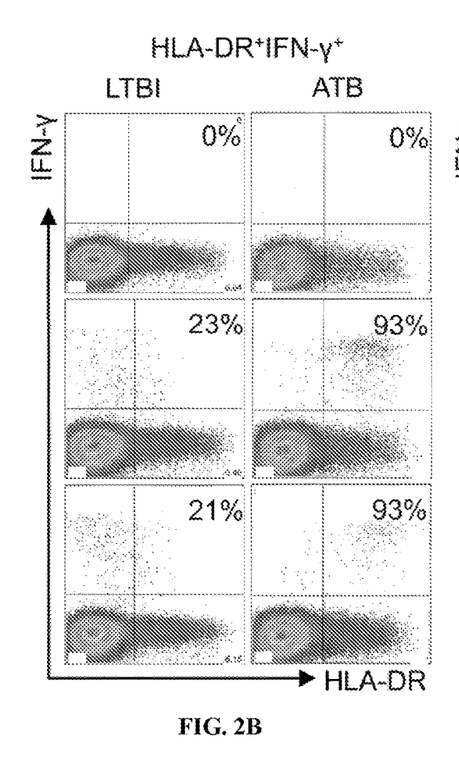
FIG. 2B shows representative flow plots for frequencies of HLA-DR$^+$IFN-$\gamma^+$ T cells.
Figure 2C:
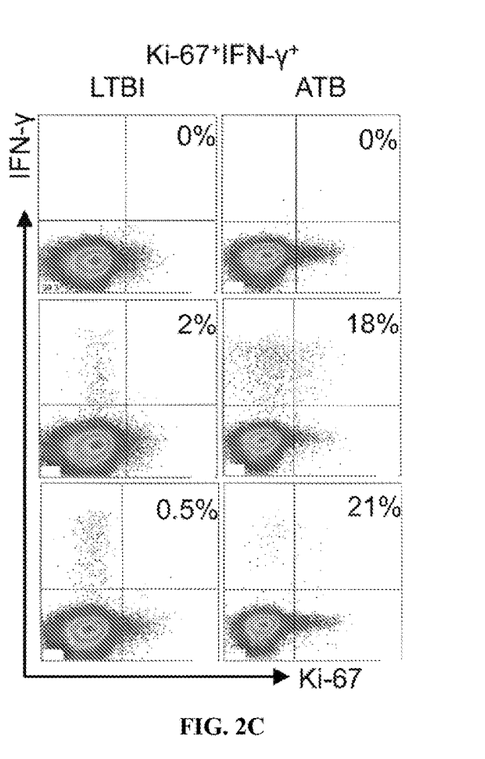
FIG. 2C shows representative flow plots for frequencies of shows Ki-67$^+$IFN-$\gamma^+$ T cells.
Figure 2D:
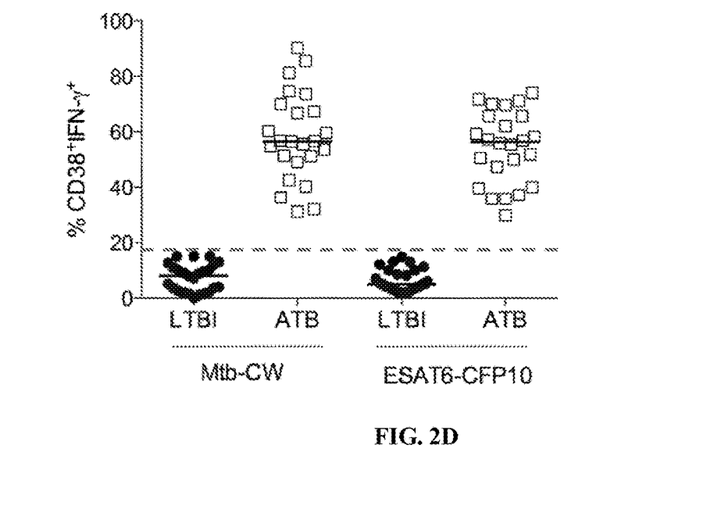
FIG. 2D shows a summary of the data of FIG. 2A representing the discrimination threshold for CD38$^+$IFN-$\gamma^+$ showing a cutoff value of 18%.
Figure 2E:
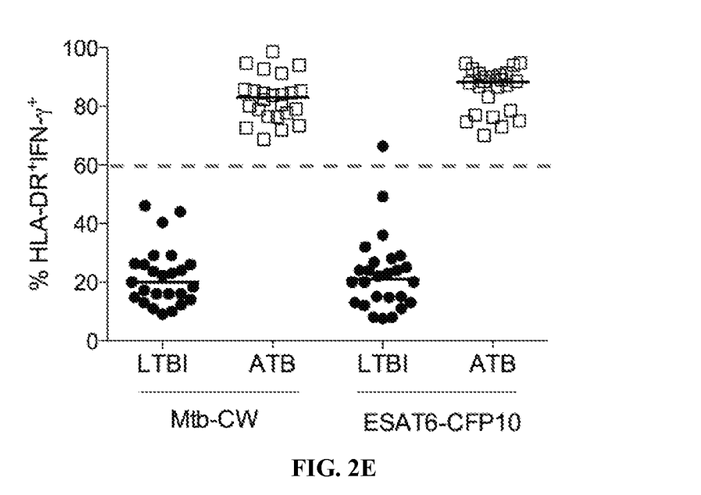
FIG. 2E shows a summary of the data of FIG. 2B representing the discrimination threshold for HLA-DR$^+$IFN-$\gamma^+$ showing a cutoff value of 60%.
Figure 2F:
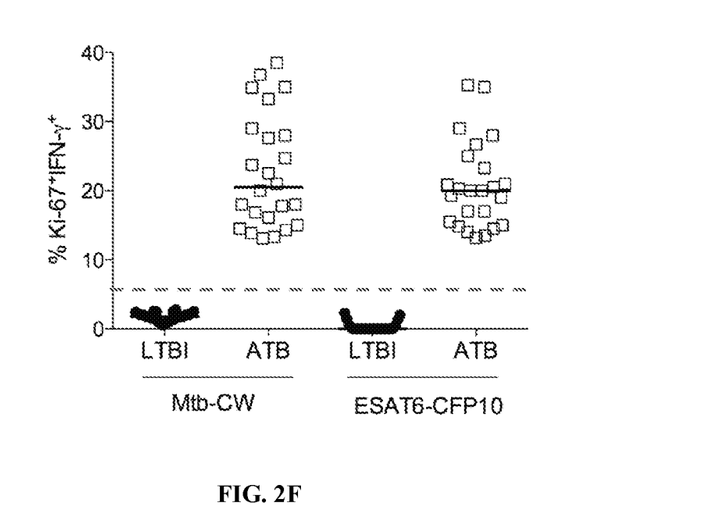
FIG. 2F shows a summary of the data of FIG. 2C representing the discrimination threshold for Ki-67$^+$IFN-$\gamma^{++}$ showing a cutoff value of 5%.
Figure 3:
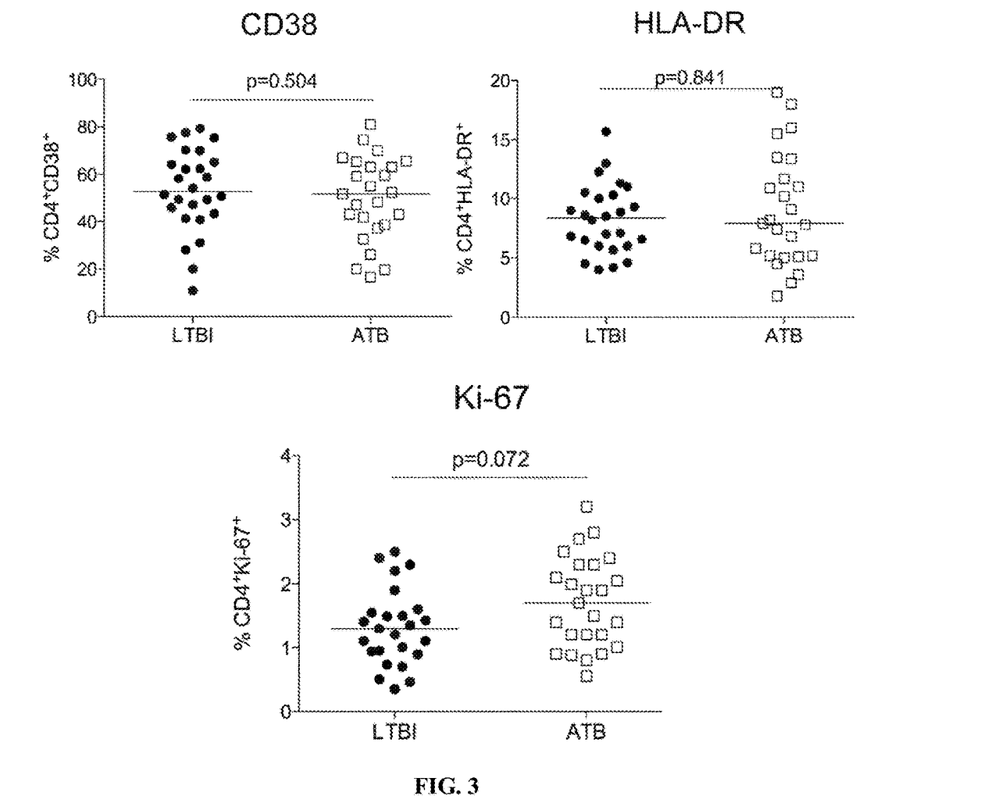
FIG. 3 shows data on CD38, HLA-DR, and Ki-67 expression on bulk CD4$^+$ T cells in the test cohort. Non-stimulated PBMCs from LTBI (n=25) and treatment-naive ATB (n=24) were analyzed for immune activation markers by flow cytometry. Mann-Whitney U test was used to compare the 2 groups.

Individuals from both the LTBI and ATB groups harbored comparable frequencies of Mtb-specific $IFN-\gamma^+CD4^+$ T cells (FIGS. 1, A and B), consistent with studies showing that Mtb-specific IFN-γ production alone does not distinguish between LTBI and ATB. In contrast, individuals with ATB had significantly higher frequencies of CW- and ESAT6/CFP10-specific $IFN-\gamma^+CD4^+$ T cells that expressed either CD38, HLA-DR, or Ki-67 (each P<0.0001), compared with LTBI (FIG. 2, A-F). These differences were restricted to Mtb-specific $CD4^+$ T cells, as expression of these markers on nonstimulated populations of T cells was similar in both groups (FIG. 3). These results show that activated and proliferating Mtb-specific $CD4^+$ T cells are preferentially associated with ATB disease.

Statistical Analyses to Determine the Predictive Value of $CD38^+IFN-\gamma^+$, $HLA-DR^+IFN-\gamma^+$, and $Ki-67^+IFN-\gamma^+CD4^+$ T Cells as Biomarkers for ATB To assess the accuracy of these markers in predicting ATB and LTBI status, receiver operating characteristic (ROC) analysis was performed in the test cohort. The AUC values for $CD38^+IFN-\gamma^+$, $HLA-DR^+IFN-\gamma^+$, and $Ki-67^+IFN-\gamma^+$ $CD4^+$ T cells were each 1.0, indicating perfect predictive power. A red, dashed line (FIG. 2, D-F) indicates the biomarker cutoff values that optimally discriminated between ATB and LTBI groups and are 18% for $CD38^+$ $IFN-\gamma^+$ (100% sensitivity and 100% specificity), 60% for $HLA-DR^+IFN-\gamma^+$ (100% sensitivity and 96% specificity), and 5% for $Ki-67^+IFN-\gamma^+$ (100% sensitivity and 100% specificity). Thus, CD38, HLA-DR, and Ki-67 on Mtb-specific $IFN-\gamma^+CD4^+$ T cells accurately distinguished active and latent TB and provided significantly greater discriminatory power for diagnosis of ATB than $CD4^+IFN-\gamma^+$ T cells alone.

Figure 4A:
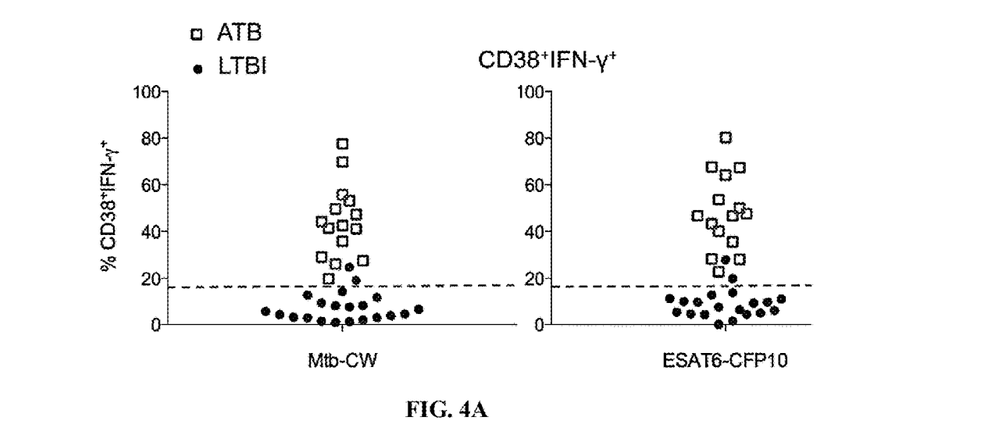
FIG. 4A shows data on the frequency of CD38$^+$IFN-$\gamma^+$ in the validation cohort. PBMCs from individuals (n=36) recruited in the Western Cape, South Africa, were stimulated with Mtb-CW antigens and ESAT6-CFP10 peptide pools or nonstimulated. The frequencies of activated Mtb-specific CD4$^+$ T cells were analyzed by flow cytometry. Summary of the data are shown for frequencies of CD38$^+$IFN-$\gamma^+$ T cells. Open squares and circles correspond to individuals with ATB and LTBI, respectively, after unblinding.
Figure 4B:
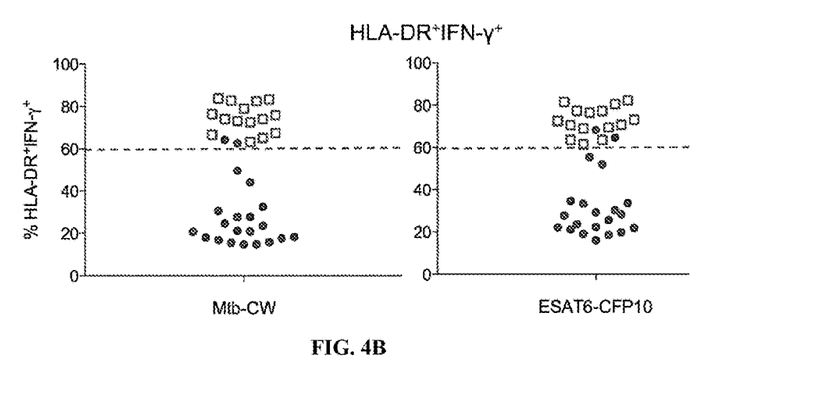
FIG. 4B shows data for frequencies of HLA-DR$^\gamma$IFN-$\gamma^+$ T cells
Figure 4C:
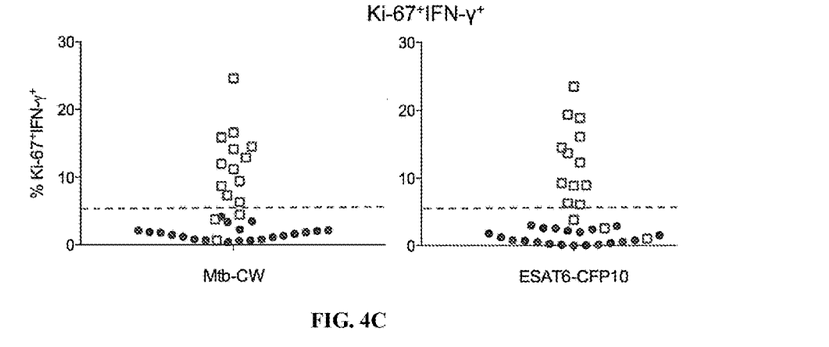
FIG. 4C shows data for frequencies of Ki-67$^+$IFN-$\gamma^+$ T cells.
Figure 5A:
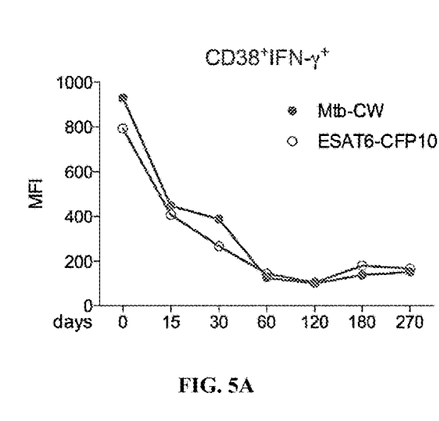
FIG. 5A shows data from MFI data of CD38$^+$ IFN-$\gamma^+$, T cells during the course of anti-TB treatment in patient P1 after stimulation with Mtb-CW (circles) or ESAT6-CFP10 (open squares).
Figure 5B:
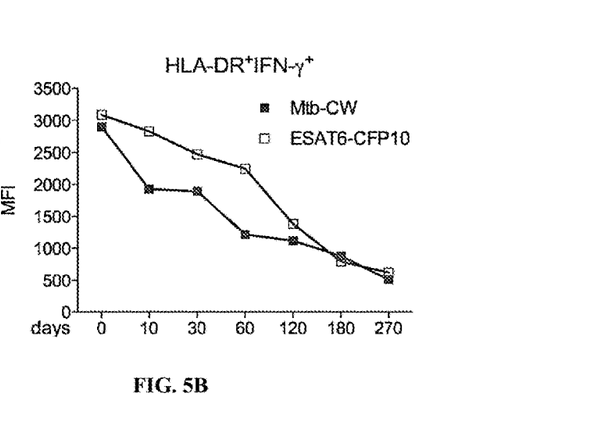
FIG. 5B shows data for HLA-DR$^\gamma$IFN-$\gamma^+$.
Figure 5C:
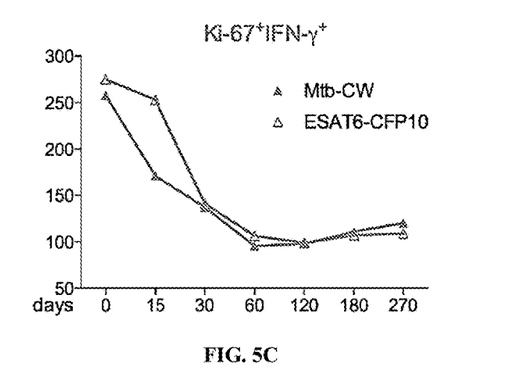
FIG. 5C shows data for Ki-67$^+$IFN-$\gamma^+$CD4$^+$.

Evaluation of the predictive value of $CD38^+IFN-\gamma^+$, $HLA-DR^+IFN-\gamma^+$, and $Ki-67^+IFN-\gamma^+CD4^+$ T cells in an independent cohort from South Africa. To explore the utility of measuring the frequencies of Mtb-specific $CD4^+$ T cells expressing CD38, HLA-DR, and Ki-67 and their respective cutoff values as diagnostic biomarkers for ATB, PBMCs were examined from an independent validation cohort from the Western Cape in South Africa. Individuals with ATB and LTBI were recruited. The investigators were blinded to the clinical diagnoses while performing laboratory analyses. PBMCs from 36 individuals with ATB or LTBI were stimulated with Mtb-CW and ESAT6-CFP10 peptide pools, and flow cytometry analyses were performed. Using the cutoffs that were statistically determined to be predictive of ATB from the test cohort data, 17 individuals had greater than 18% frequencies of $CD38^+IFN-\gamma^+$, 17 individuals had greater than 60% frequencies of $HLA-DR^+IFN-\gamma^+$, and 12 individuals had greater than 5% frequencies of $Ki-67^+$ IFN-γ+ (FIG. 4, A-C). After unblinding, it was determined that 15 out of the 17 individuals classified as ATB by CD38+IFN-γ+ and HLA-DR+IFN-γ+ had clinically confirmed ATB, while all 12 individuals classified as ATB by Ki-67+IFN-γ+ had clinically confirmed ATB (FIG. 4, A-C). Similarly, based on the cutoffs that were statistically determined to be predictive of LTBI from the test cohort, 19 individuals had frequencies of CD38+IFN-γ+ that were less than 18%, 19 individuals had frequencies of HLA-DR+IFN-γ+ that were less than 60%, and 24 individuals had frequencies of Ki-67+IFN-γ+ that were less than 5%. After unblinding, all 19 individuals classified as LTBI by CD38+IFN-γ+ and HLA-DR+IFN-γ+ and 21 out of 24 individuals classified as LTBI by Ki-67+IFN-γ+ were confirmed to be LTBI (FIG. 5, A-C). Overall, CD38+IFN-γ+ and HLA-DR+IFN-γ+ predicted the clinical diagnosis of ATB in 100% of the cases, while Ki-67+IFN-γ+ predicted 80% of the cases.

Decreases in the Frequencies of Activated Mtb-Specific CD4+ T Cells are Associated with Smear and Culture Conversion during Anti-TB Treatment To determine whether Mtb-specific CD38+IFN-γ+, HLA-DR+IFN-γ+, or Ki-67+IFN-γ+CD4+ T cells correlated with response to treatment and mycobacterial load, longitudinal studies of sputum-positive pulmonary ATB patients were performed with drug-susceptible TB (n=10) who were enrolled prior to initiation of treatment and followed during and after successful completion of treatment. Frequencies of CD38+IFN-γ+, HLA-DR+IFN-γ+, and Ki-67+IFN-γ+CD4+ T cells were assessed at baseline (time 0) and at multiple time points after treatment initiation. Baseline diagnosis by sputum acid-fast bacilli (AFB) smear and culture is indicated for each patient, and sputum was monitored for AFB smear and culture conversion during treatment. In a representative patient, P1, frequencies of CD38+IFN-γ+, HLA-DR+IFN-γ+, and Ki-67+IFN-γ+ T cells decreased over the course of treatment in response to stimulation with Mtb-CW and ESAT6-CFP10 peptides, while frequencies of CD45RA-IFN-γ+ T cells remained unchanged. This reflected decreasing bacterial burdens, as evidenced by sputum smear and culture conversion at 2 months. Similar results were seen when the data were expressed as median fluorescence intensity (MFI) (FIG. 5A-C). These trends were observed for all 10 patients studied, suggesting that decreases in the frequencies of Mtb-specific CD4+ T cells expressing CD38, HLA-DR, or Ki-67 are associated with treatment response in patients with drug-susceptible TB. Notably, while patients P4 and P5 were smear negative at day 45, they remained culture positive and had higher than cutoff values for the host markers studied, confirming the relative imprecision of smears for monitoring treatment and highlighting greater sensitivity of culture and host markers for assessing Mtb clearance during treatment.

Figure 6A:
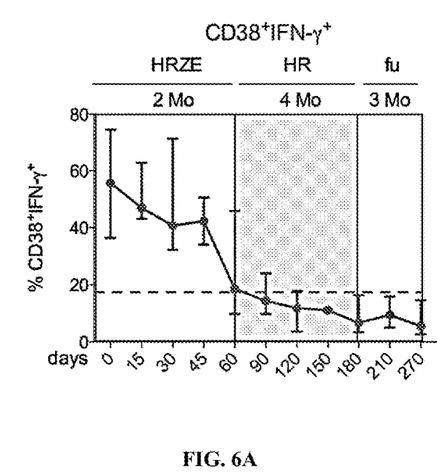
FIG. 6A shows data on longitudinal monitoring during anti-TB treatment in ATB patients. Treatment response and culture conversion were monitored in sputum by smear microscopy and culture. Cumulative data for patients are presented for CD38$^+$IFN-$\gamma^+$ T cells over the course of anti-TB treatment. The 2-month intensive phase (HRZE), 4-month continuation phase (HR), and follow-up (fu) post-treatment completion are indicated.
Figure 6B:
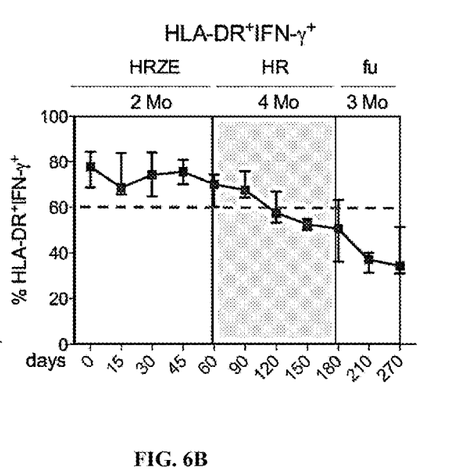
FIG. 6B shows cumulative data in patients for HLA-DR$^+$ IFN-$\gamma^+$.
Figure 6C:
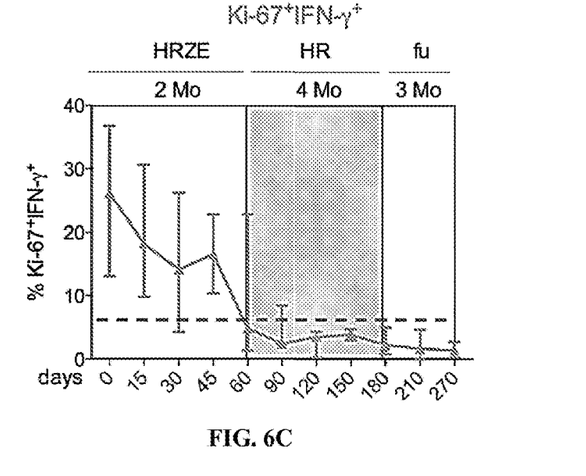
FIG. 6C shows cumulative data in patients for Ki-67$^+$ IFN-$\gamma^+$.

The standard treatment regimen for drug-susceptible TB consists of a 2-month intensive phase with isoniazid, rifampicin, pyrazinamide, and ethambutol (HRZE), followed by a 4-month continuation phase with isoniazid and rifampicin (HR). Conversion to a negative sputum culture at 2 months after treatment initiation is currently the most objective indicator of response to treatment. FIG. 6, A-C, indicates the cumulative data for all 10 patients. FIG. 6B shows that at the 2-month (60 days) time point following the HRZE phase, the median frequencies of CD38+IFN-γ+CD4+ T cells decreased significantly compared with baseline (P=0.002) and approached the cutoff value of 18% for discriminating between LTBI and ATB. Similar trends were observed for HLA-DR+IFN-γ+ (P=0.01) and Ki-67+IFN-γ (P=0.003) CD4+ T cells (FIGS. 6, B and C). These frequencies continued to decline, falling below the cutoffs during the 4-month (180 days) HR phase and posttreatment time points (FIG. 6, A-C).

Figure 7A:
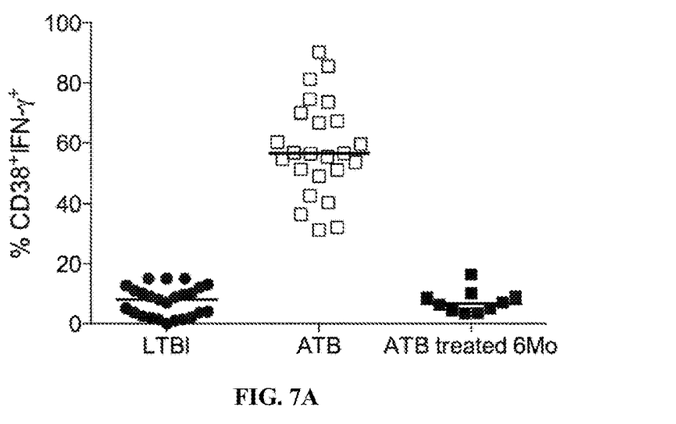
FIG. 7A shows data indicating frequencies of activated Mtb-specific CD4$^+$ CD38$^+$IFN-$\gamma^+$ T cells in PBMCs from individuals with LTBI (n=25) and treatment-naive ATB (n=24) as well as those who received 6 months of anti-TB treatment (ATB treated 6 mo; n=10).
Figure 7B:
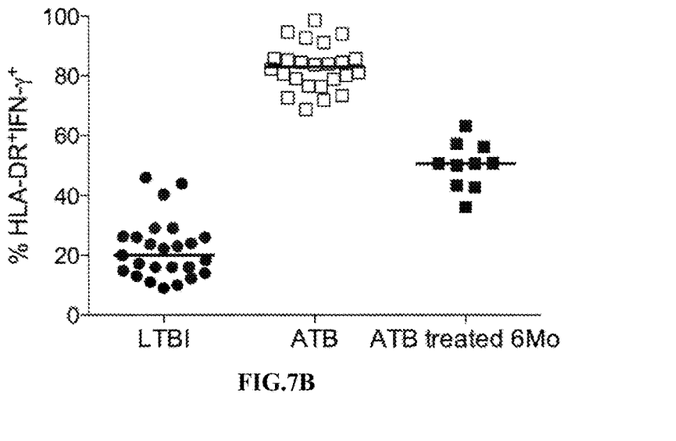
FIG. 7B shows data for HLA-DR$^+$IFN-$\gamma^+$.
Figure 7C:
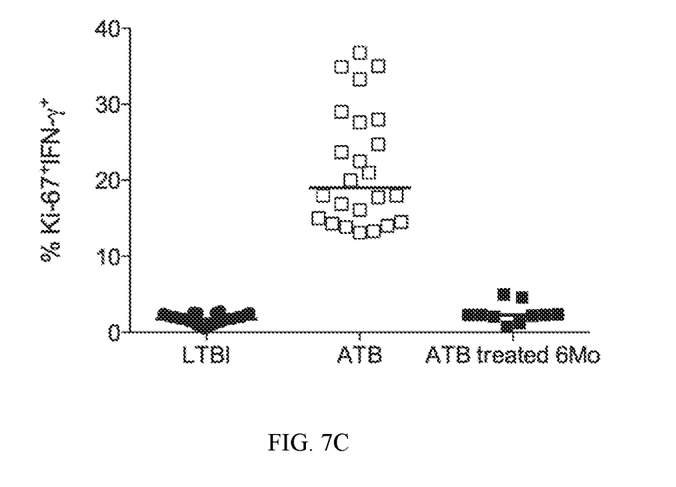
FIG. 7C shows data for Ki-67$^+$IFN-$\gamma^+$.

Frequencies of Activated Mtb-Specific CD4+T in Individuals with Clinically Resolved TB are Comparable to Those in Individuals with LTBI The frequencies of CD38+IFN-γ+, HLA-DR+IFN-γ+, and Ki-67+IFN-γ+CD4+ T cells were compared in individuals with LTBI and ATB as well as those who had successfully completed the 6-month standard regimen of anti-TB treatment (ATB treated 6 mo). Frequencies of Mtb-specific IFN-γ+CD4+ T cells expressing CD38, HLA-DR, and Ki-67 were significantly lower (P<0.0001) in the treated ATB group compared with individuals with untreated ATB and reached or approached frequencies seen in the LTBI group (FIG. 7, A-C). While frequencies of CD38+IFN-γ and Ki-67+IFN-γ were indistinguishable in treated ATB and LTBI groups, HLA-DR+IFN-γ remained higher in treated ATB groups than in LTBI. Consistent with reports, frequencies of total CD4+IFN-γ T cells alone did not distinguish ATB patients from those who had successfully completed treatment.

Figure 8A:
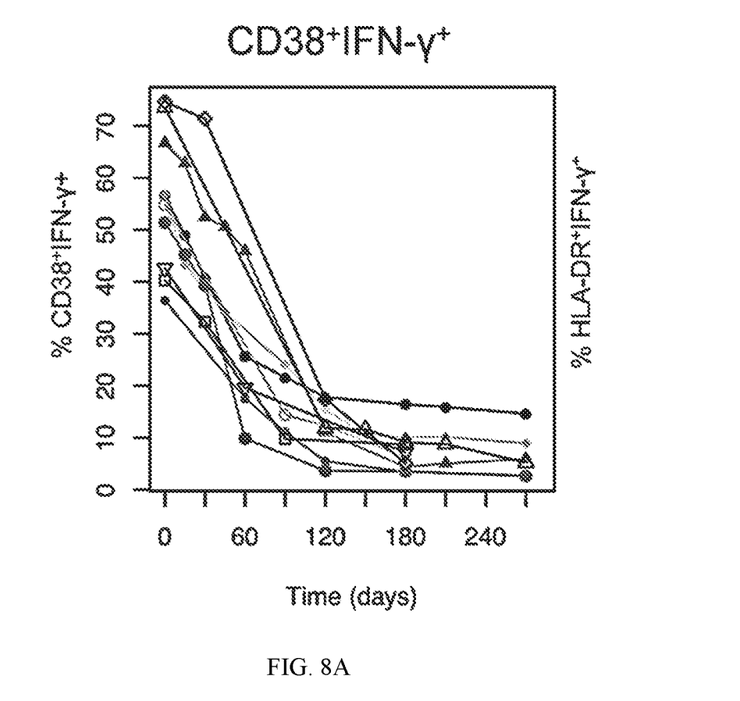
FIG. 8A shows a graphical representation of linear mixed-effects modeling of anti-TB treatment response to show that frequencies of CD38$^+$IFN-$\gamma^+$ T cells decreased significantly in response to anti-TB treatment in each patient with drug-susceptible TB.
Figure 8B:
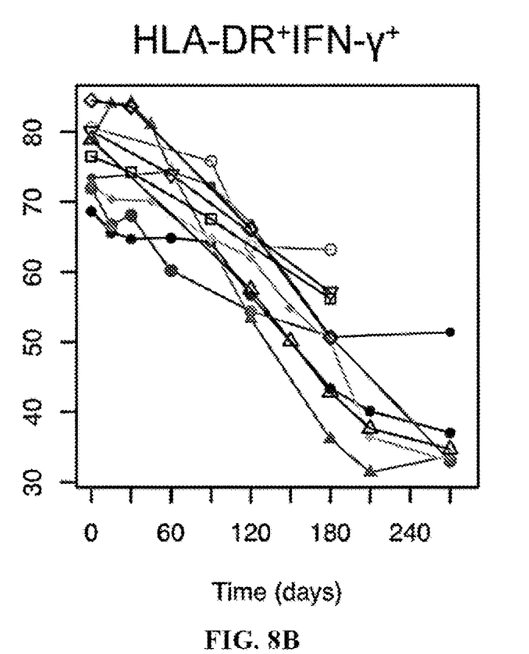
FIG. 8B shows data for HLA-DR$^+$IFN-$\gamma^+$.
Figure 8C:
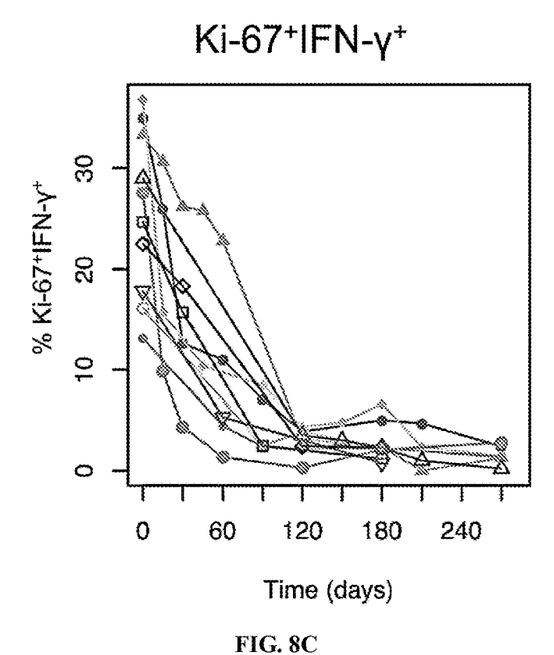
FIG. 8C shows data for Ki-67$^+$IFN-$\gamma^+$.

Development of a Linear Mixed-Effects Model for Modeling Response to Anti-TB Treatment To model response to therapy from longitudinal data of ATB patients, a linear mixed-effects model was used. This enables one to statistically assess whether expression of the candidate biomarkers, CD38, HLA-DR, and Ki-67, on IFN-γ+CD4+ T cells correlated with treatment response over time for each patient by fitting the longitudinal data to a linear mixed-effects model and accounting for the correlation of repeated measurements from the same patient (FIG. 8). The "lme" function in R version 2.15.1 was used to analyze the longitudinal data and account for repeated measurements from the same patient. To determine whether there was a decrease of an individual biomarker over time, the model, $Y_{it}=b_0+b_1 \times time_t+b_i+e_{it}$, was used where $Y_{it}$ is the value of the biomarker for the $i^{th}$ patient at the $t^{th}$ time point, time t is the day of the $t^{th}$ time point, $b_i$ is a random effect that follows $N(0, s_b^2)$, and $e_{it}$ is an error term that follows $N(0, s^2)$ and is independent of bi. $H_0: b_1=0$ against $H_0: b_1<0$ was tested using the Wald test. P<0.05 was considered statistically significant. These analyses revealed that there was a significant decrease over time for each of the markers (P<0.0001), indicating that CD38+IFN-γ+, HLA-DR+IFN-γ+, and Ki-67+IFN-γ+CD4+ T cells each correlated with response to treatment (FIG. 8).

Methods

The presence of CD4+IFN-γ+ T cells in PBMCs from both ATB and LTBI groups was assessed by flow cytometry and intracellular cytokine staining (ICS) following stimulation with Mtb-CW antigens and ESAT6 and CFP10 peptide pools. Out of the 26 ATB patients, 2 did not show reactivity to ESAT6/CFP10 peptide pools and were excluded from the study analysis.

PBMC Isolation, Antigens, and Peptides for Cell Stimulations

Blood samples from the Georgian cohort were collected from all subjects at baseline and longitudinal time points. PBMCs were isolated from blood using cell preparation tubes (CPT, BD Biosciences) and cryopreserved in 90% fetal FBS (Hyclone) and 10% dimethyl sulfoxide (Sigma-Aldrich). PBMCs from the South African cohort were isolated using Ficoll-Hypaque (Sigma-Aldrich) in South Africa and cryopreserved at 180° C. anywhere from 4 months to 4 years after collection. Stimulation of PBMCs was performed at the Emory Vaccine Center with Mtb-CW antigens (NIH- TBVRM contract, Colorado State University) and ESAT6-CFP10 peptide pools, which were composed of 15 mers with 11 amino-acid overlap (Gene-med Synthesis Inc.).

Flow Cytometry and Staining

For ICS, cryopreserved PBMCs were rested overnight at 37° C., 5% CO2, in RPMI 1640 medium (Lonza) containing 10% FBS, 2 mM glutamine, 100 IU/ml penicillin, and 100 μg/ml streptomycin. The viability of the lymphocytes was 75% to 95%. PBMCs (1 to 2×106) were each stimulated with CW antigens (10 μg/ml) and ESAT6 and CFP10 peptide pools (10 μg/ml) for 2 hours followed by the addition of Brefeldin A (10 μg/ml) (BD Biosciences) and further incubated for 16 hours. PBMCs were stained for dead cells with LIVE/DEAD Fixable Yellow Dead Cell Stain (Life Technologies) at the beginning and then surface stained with appropriate antibodies: CD4 PerCp-Cy5.5 (clone L200), CD8 V500 (clone SK1), HLA-DR PE-Cy7 (clone L243), all from BD Biosciences; CD38 ECD (clone LS198.4.3) from Beckman-Coulter; and CD45RA BV711 (clone HI100) from Biolegend. They were then permeabilized with Cytofix/Cytoperm Kit (BD Biosciences), stained intracellularly with appropriate antibodies (IFN-γ Alexa Fluor 700 [clone B27], Ki-67 PE [clone B56], and CD3 APC-H7 [clone UCHT1], all from BD Biosciences) and fixed with 1% paraformaldehyde before acquisition on an LSR-II system (BD Biosciences). Flow cytometry data were analyzed with FlowJo software (Tree Star Inc.). Positive Mtb-specific CD4$^+$ T cell responses were defined by a frequency of CD4$^+$IFN-γ$^+$ of 0.05% or more.

The invention claimed is:

1. A method of diagnosing and treating a subject with tuberculosis comprising the steps of,
    measuring a pool of CD4 IFN-γ cells for cells that also express CD38, HLA-DR, and Ki-67 providing a measurement;
    associating an increased measurement of CD4 IFN-γ cells that also express CD38, HLA-DR, Ki-67, compared to a control, as an indication that the subject has active tuberculosis infection, providing a subject diagnosed with an active tuberculosis infection,
    wherein the increased measurement of CD4 IFN-γ cells that also express CD38, HLA-DR, Ki-67, compared to a control is a quantification that,
        greater than 18% of the CD4 IFN-γ cells also express CD38;
        greater than 60% of the CD4 IFN-γ cells also express HLA-DR; and
        greater than 5% of the CD4 IFN-γ cells also express Ki-67; and
    administering to the subject diagnosed with an active tuberculosis infection an aggressive tuberculosis treatment.

2. The method of claim 1, wherein the aggressive tuberculosis treatment comprises administering a combination of more than two antibacterial agents.

3. The method of claim 1, wherein the aggressive tuberculosis treatment comprises administering a combination of isoniazid, rifampicin, pyrazinamide, and ethambutol.

4. The method of claim 1, further comprising the steps of,
    measuring a second pool of CD4 IFN-γ cells for the quantity of cells that also express CD38, HLA-DR, and Ki-67;
    associating a deceased measurement of CD4 IFN-γ cells that also express CD38, HLA-DR, Ki-67, compared to the increased measurement, as an indication that the subject has a latent tuberculosis infection, providing a subject diagnosed with a latent tuberculosis infection; and
    administering to the subject diagnosed with a latent tuberculosis infection a less aggressive tuberculosis treatment.

5. The method of claim 4, wherein the less aggressive tuberculosis treatment is only one or not more than a combination of two antibacterial agents.

6. The method of claim 4, wherein the less aggressive tuberculosis treatment is a combination of only isoniazid and rifampicin.

7. The method of claim 1, wherein the measurement, quantification, or indication is recorded on a computer readable medium.

8. The method of claim 7, wherein the measurement, quantification, or indication is communicated to a medical professional or the subject.

* * * * *